US00PP19448P2

(12) United States Plant Patent
Takahata et al.

(10) Patent No.: US PP19,448 P2
(45) Date of Patent: Nov. 11, 2008

(54) ***IPOMOEA* PLANT NAMED 'KYUIKUKAN 2'**

(50) Latin Name: *Ipomoea batatas*
Varietal Denomination: Kyuikukan 2

(75) Inventors: Yasuhiro Takahata, Miyakonojo (JP); Hiroki Nakayama, Miyakonojo (JP); Yoshinori Nakazawa, Kumamoto (JP); Yumi Kai, Miyakonojo (JP); Tetsufumi Sakai, Miyakonojo (JP); Kazunari Iwaki, Kanagawa (JP); Masaru Yoshinaga, Miyakonojo (JP); Masaru Tanaka, Miyakonojo (JP); Toru Kumagai, Tsukuba (JP); Kenji Katayama, Miyakonojo (JP); Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/800,772

(22) Filed: May 7, 2007

(51) Int. Cl.
*A01H 5/00* (2006.01)

(52) U.S. Cl. ..... Plt./226

(58) Field of Classification Search ..... Plt./226, Plt./22
See application file for complete search history.

*Primary Examiner*—Annette H Para
(74) *Attorney, Agent, or Firm*—C. A. Whealy

(57) ABSTRACT

A new and distinct cultivar of *Ipomoea* plant named 'Kyuikukan 2', characterized by its compact and outwardly trailing growth habit; and bright green-colored young foliage and dark purple-colored mature foliage.

1 Drawing Sheet

Botanical designation: *Ipomoea batatas.*
Cultivar denomination: 'Kyuikukan 2'.

BACKGROUND OF THE INVENTION

The present invention relates to a new and distinct cultivar of *Ipomoea*, botanically known as *Ipomoea batatas*, and hereinafter referred to by the name 'Kyuikukan 2'.

The new *Ipomoea* is a product of a planned breeding program conducted by the Inventors in Miyazaki, Japan. The objective of the breeding program is to create new compact *Ipomoea* cultivars with attractive foliage shape and coloration.

The new cultivar originated from a cross-pollination made by the Inventors in June, 2001 of a proprietary *Ipomoea batatas* selection identified as code number 99US-OR, not patented, as the female, or seed, parent with a mixture of pollen from six proprietary selections of *Ipomoea batatas,* not patented. The cultivar Kyuikukan 2 was discovered and selected by the Inventors as a single plant within the progeny of the stated cross-pollination in a controlled environment in Miyazaki, Japan.

Asexual reproduction of the new *Ipomoea* by terminal cuttings in a controlled environment in Miyazaki, Japan since December 2005, has shown that the unique features of this new *Ipomoea* are stable and reproduced true to type in successive generations.

SUMMARY OF THE INVENTION

The cultivar Kyuikukan 2 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kyuikukan 2'. These characteristics in combination distinguish 'Kyuikukan 2' as a new and distinct cultivar of *Ipomoea:*

1. Compact and outwardly trailing growth habit.
2. Bright green-colored young foliage and dark purple-colored mature foliage.

Plants of the new *Ipomoea* can be compared to plants of the female parent selection. Plants of the new *Ipomoea* differ from plants of the female parent selection in the following characteristics:

1. Plants of the new *Ipomoea* are more compact than plants of the female parent selection.
2. Plants of the new *Ipomoea* have shorter internodes than plants of the female parent selection.
3. Plants of the new *Ipomoea* have larger leaves than plants of the female parent selection.
4. Plants of the new *Ipomoea* are more high temperature tolerant than plants of the female parent selection.

Plants of the new *Ipomoea* differ primarily from plants of the pollen parent selections primarily in leaf coloration.

Plants of the new *Ipomoea* can be compared to plants of the *Ipomoea batatas* cultivar Sweet Caroline Purple, disclosed in U.S. Plant Pat. No. 14,912. In side-by-side comparisons conducted in Shiga, Japan, plants of the new *Ipomoea* differed from plants of the cultivar Sweet Caroline Purple in the following characteristics:

1. Plants of the new *Ipomoea* were shorter than plants of the cultivar Sweet Caroline Purple.
2. Plants of the new *Ipomoea* had longer internodes than plants of the cultivar Sweet Caroline Purple.
3. Plants of the new *Ipomoea* had larger leaves and longer petioles than plants of the cultivar Sweet Caroline Purple.
4. Leaves of plants of the new *Ipomoea* had sagittate bases whereas leaves of plants of the cultivar Sweet Caroline Purple had acute bases.

BRIEF DESCRIPTION OF THE PHOTOGRAPHS

The accompanying colored photographs illustrate the overall appearance of the new *Ipomoea*, showing the colors as true as it is reasonably possible to obtain in colored reproductions of this type. Colors in the photographs may differ slightly from the color values cited in the detailed botanical description which accurately describe the colors of the new *Ipomoea*.

The photograph at the top of the sheet comprises a side perspective view of a typical plant of 'Kyuikukan 2' grown in a container.

The photograph at the bottom of the sheet comprises a close-up view of typical leaves of 'Kyuikukan 2'.

DETAILED BOTANICAL DESCRIPTION

The photographs and following observations, measurements and values describe plants grown in Shiga, Japan in a polyethylene-covered greenhouse during the summer under conditions which closely approximate commercial production. During the production of the plants, day temperatures were about 28° C. and night temperatures were about 18° C. Plants were about four months old when the photographs and the description were taken. In the detailed description, color references are made to The Royal Horticultural Society Colour Chart, 2001 Edition, except where general terms of ordinary dictionary significance are used.

Botanical classification: *Ipomoea batatas* cultivar Kyuikukan 2.

Parentage:

*Female, or seed, parent.*—Proprietary seedling selection of *Ipomoea batatas* identified as code number 99US-OR, not patented.

*Male, or pollen, parent.*—A mixture of pollen from six proprietary selections of *Ipomoea batatas,* not patented.

Propagation:

*Type.*—By terminal cuttings.

*Time to initiate roots.*—About three days at temperature of 20° C. to 25° C.

*Time to produce a rooted young plant.*—About four weeks at temperatures of 20° C. to 25° C.

*Root description.*—Thick, fleshy. Development of tubers, ellipsoidal in shape and white in color, has been observed.

Plant description:

*Plant habit.*—Compact and outwardly trailing plant habit. Freely branching habit; pinching enhances lateral branch development; vigorous growth habit.

*Plant height.*—About 15 cm.

*Plant diameter.*—About 33.6 cm.

Lateral branch description:

*Length.*—About 12.4 cm.

*Diameter.*—About 3.2 mm.

*Internode length.*—About 3.3 cm.

*Strength.*—Strong.

*Texture.*—Pubescent.

*Color.*—187A.

Foliage description:

*Arrangement.*—Alternate, simple.

*Length.*—About 12.7 cm.

*Width.*—About 12.3 cm.

*Shape.*—Roughly palmate.

*Apex.*—Acute.

*Base.*—Sagittate.

*Margin.*—Entire; deeply lobed.

*Texture, upper and lower surfaces.*—Pubescent.

*Venation pattern.*—Palmate.

*Color.*—Developing foliage, upper and lower surfaces: 144A; venation, 144A. Fully expanded foliage, upper surface: Close to N186A; venation, close to N186A. Fully expanded foliage, lower surface: Close to 187C; venation, close to 187C.

*Petiole.*—Length: About 10.8 cm. Diameter: About 2.8 mm. Texture, upper and lower surfaces: Smooth, glabrous. Color, upper surface: 144A. Color, lower surface: 187A.

Flower description:

Plants of the new *Ipomoea* do not develop flowers.

Temperature tolerance:

Plants of the new *Ipomoea* have been observed to tolerate temperatures from about 5° C. to about 35° C.

Pathogen/pest resistance:

Plants of the new *Ipomoea* have not been observed to be resistant to pests and pathogens common to *Ipomoea*.

It is claimed:

1. A new and distinct *Ipomoea* plant named 'Kyuikukan 2' as illustrated and described.

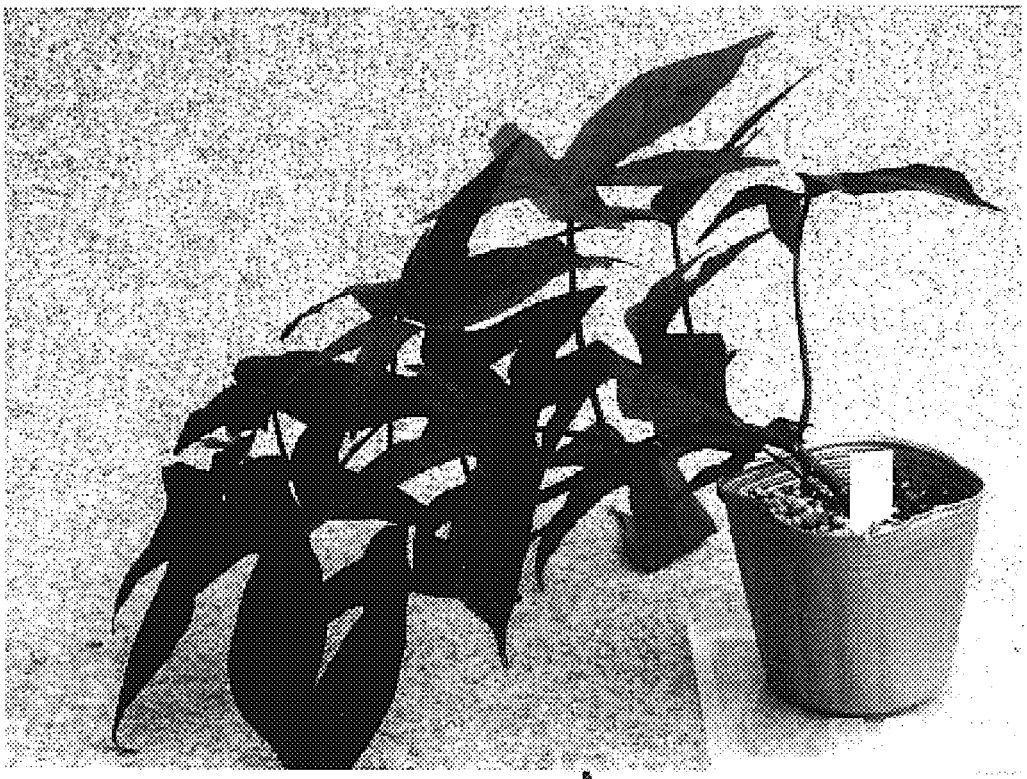
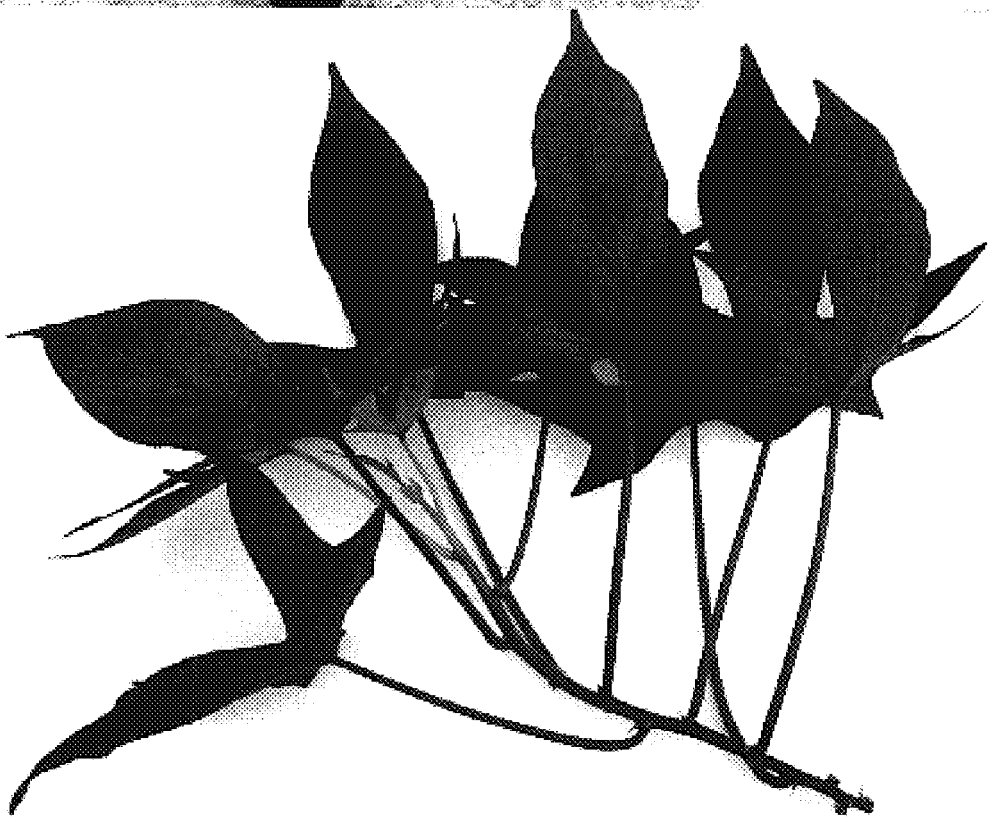

* * * * *